United States Patent
Stein et al.

[11] Patent Number: 5,899,082
[45] Date of Patent: May 4, 1999

[54] METHOD AND APPARATUS FOR ODOR ELIMINATION IN VEHICLE AIR CONDITIONING SYSTEMS

[76] Inventors: Myron Stein, 31412 Flying Cloud, Leguna Niguel, Calif. 29677; William Brown, 540 E. South St., Bryan, Ohio 43506; Ron Viskil, 1 W. Denijslaan, 2101EN Heemstede, Netherlands; Glenn R. Reddington, 223 Wimbedon Lake Dr., Plantation, Fla. 33324

[21] Appl. No.: 08/933,601

[22] Filed: Sep. 18, 1997

[51] Int. Cl.$^6$ ...................................................... F25D 21/00
[52] U.S. Cl. .............................. 62/133; 62/150; 62/158; 62/182; 62/282; 62/244
[58] Field of Search .............................. 62/133, 158, 180, 62/182, 244, 278, 282, 82, 234, 151, 155, 150

[56] References Cited

U.S. PATENT DOCUMENTS

| | | | |
|---|---|---|---|
| 2,953,908 | 9/1960 | Petrone et al. | 62/158 |
| 4,604,873 | 8/1986 | Ohashi et al. | 62/158 |
| 4,742,763 | 5/1988 | Holter et al. | 98/2.01 |
| 4,744,289 | 5/1988 | Holter et al. | 98/2.01 |
| 5,078,046 | 1/1992 | Mascolo et al. | 454/157 |
| 5,259,813 | 11/1993 | Abthoff et al. | 454/75 |
| 5,335,690 | 8/1994 | Worth | 137/268 |
| 5,385,028 | 1/1995 | Gavlak | 62/81 |

*Primary Examiner*—Harry B. Tanner
*Attorney, Agent, or Firm*—Womble Carlyle Sandridge & Rice

[57] ABSTRACT

A method of drying condensate from the heat exchanger of a vehicle's air conditioning system after operation in order to thwart odor buildup is provided. The method comprises first determining that the engine of the vehicle has been switched off and that the air conditioning system of the vehicle was in operation prior to the engine being switched off. If these two conditions are met, the blower of the vehicle's air conditioning system is operated on a predetermined time schedule to draw air through the heat exchanger and through the air conditioning duct work to dry condensate from the heat exchanger and from interior surfaces of the duct work. In this way, the growth of fungus and bacteria that cause odor is thwarted.

19 Claims, 3 Drawing Sheets

METHOD AND APPARATUS FOR ODOR ELIMINATION IN VEHICLE AIR CONDITIONING SYSTEMS

TECHNICAL FIELD

The present invention relates generally to automotive air conditioning systems and more particularly to the prevention of moisture buildup within such air conditioning systems with the goal of eliminating the propagation of fungus and bacteria and the odor that results therefrom.

BACKGROUND OF THE INVENTION

Automotive air conditioning systems are provided in most vehicles to cool the passenger compartment of the vehicle during hot weather. In general, automotive air conditioning systems comprise a compressor coupled to the engine that compresses a refrigerant to its liquid state. The compressed liquid refrigerant is then delivered to a heat exchanger within the duct work of the air conditioning system, where it is allowed to expand and cool the exchanger. A blower forces air across the heat exchanger and into the passenger compartment of the vehicle. As the air passes through the cold heat exchanger, it is cooled and the latent heat that was contained in the air is transferred to the refrigerant within the heat exchanger. Thus, the passenger compartment receives cool air. The heated refrigerant is then passed through a radiator where it is cooled and then delivered back to the compressor where the cycle begins anew.

As warm air passes through the heat exchanger of an automotive air conditioning system to be cooled, water vapor contained in the warm air condenses on the surfaces of the heat exchanger. During normal operation of the vehicle, the water vapor that condenses on the heat exchanger simple runs to the bottom of the exchanger and is drained from the air conditioning system onto the roadway. However, when the vehicle's engine is shut off and the air conditioner is no longer in operation, the water that has condensed on the heat exchanger begins to evaporate within the duct work of the air conditioning system and, as a result, a damp dank atmosphere is created. Such an atmosphere is ideal for the growth of mold, mildew, and other fungus and bacteria within the duct work of the system and particularly on the moist and wet surfaces of the heat exchanger. The growth of such organisms, in turn, results in a stale and unpleasant odor within the passenger compartment itself and can lead to airborne spores and other organisms that are unhealthy for the occupants of the vehicle.

In the past, there have been attempts to address the problems of fungus and bacteria buildup within automotive air conditioning systems. U.S. Pat. No. 5,385,028 of Gavlak, for example, discloses a method of eliminating odor in a heat pump system of a vehicle. The Gavlak method comprises determining when operation of the vehicle has been discontinued by sensing the removal of the ignition key from the ignition switch and by sensing the release of pressure from the seats of the vehicle indicating that passengers have disembarked. When these two criteria have been met, a reversing valve is activated to reverse the flow of refrigerant through the heat pump system of the vehicle in a direction opposite to the direction in which it had been flowing. As the refrigerant flows in the reverse direction, the blower of the system is activated to blow moisture off of internal surfaces of the system. The reversing of refrigerant flow tends to heat the heat exchanger, thereby accelerating the evaporation of moisture therefrom, whereupon blower operation tends to remove the moisture from the system.

While the method and apparatus of Gavlak may function adequately to dry a vehicle air conditioning system, it is nevertheless plagued with a variety of problems and shortcomings inherent in its design. One of the main problems with the Gavlak solution resides in its complexity. For example, in order to operate, the Gavlak device must be coupled to the ignition switch of the vehicle in such a way that removal of the ignition key can be detected. Furthermore, Gavlak requires that pressure sensors be installed in the seats of the vehicle in order to determine when passengers have disembarked from the vehicle. In addition, the device of Gavlak must be coupled to a reversing valve in order to reverse the coolant through the heat pump system of the vehicle and must also be coupled to the blower of the system so that the blower can be operated under the appropriate circumstances.

The complexity of Gavlak is particularly troublesome in cases where the device of Gavlak is to be retrofitted onto vehicles that were not provided from the factory with such functions. In these instances, proper installation of the Gavlak device is so complex that many average mechanics are unable to complete the installation and specially trained mechanics who usually work directly for automotive companies are required. Because of such labor costs and because of the complexity of the Gavlak device including its various sensors and switches, the Gavlak method is expensive to implement such that most vehicle owners will not afford to have the device installed.

General Motors also provides an air conditioner delay blower control module that can be installed as a retrofit on GM vehicles. However, this device, like that disclosed in Gavlak, is extremely complex and requires electrical connection to no less than seven or eight components of the vehicle's electrical and air conditioning systems. Thus, for the same reasons discussed above, the preexisting General Motors device is also prohibitively complex and expensive.

Accordingly, there exists a continuing and heretofore unaddressed need for a reliable method of eliminating the growth of fungus such as mold, mildew, and other organisms within a vehicle's air conditioning system to eliminate the odor and other undesirable consequences thereof. Such a method and apparatus should be relatively inexpensive so that it is affordable as a retrofit on existing vehicles, should operate reliably and conveniently for many years, and should be extremely simple to install so that even the most modest auto mechanic can provide installation services. It is to the provision of such a method and apparatus that the present invention is primarily directed.

SUMMARY OF THE INVENTION

Briefly described, the present invention, in one preferred embodiment thereof, comprises a method and apparatus for eliminating stale odors related to the growth of mold, mildew, and other organisms within a vehicle's air conditioning system. The method of this invention comprises determining that the engine of the vehicle has been switched off after operation. This determination is made by sensing the voltage of the vehicle's ignition system and determining that the engine has been switched off if the voltage falls below 13 volts. Once it is determined that the engine has been switched off, it is next determined that the air conditioning system of the vehicle was in operation while the engine was running. This determination is made in the present invention by sensing the ambient temperature in the vicinity of the vehicle and making the determination that the air conditioning system was in operation if the ambient temperature is above 60 degrees. In most instances, this is a valid assumption since the vehicle's air conditioning system will usually not be operated when the ambient temperature is below 60 degrees.

If it is determined that the engine of the vehicle has been switched off and the air conditioning system of the vehicle was in operation, then the method of the present invention further comprises the step of operating the blower of the vehicle's air conditioning system on a predetermined time schedule to draw air through the system, through the heat exchanger of the system, and out the air conditioning vents to dry condensate from surfaces within the air conditioning system. In one preferred embodiment, the method comprises delaying for an initial 30 minute period to allow condensate within the system to evaporate. The blower is then operated for 10 seconds to remove the evaporated condensate and a 10 minute delay is initiated to permit further evaporation of the condensate. This cycle is repeated for a predetermined number of times until the condensed moisture on the heat exchanger surface and within the air conditioning system has been dried and removed. Once the drying cycle is complete, the method of the present invention stops and waits for the engine of the vehicle to start again to reinitiate the entire process.

Accordingly, a greatly improved method and apparatus is now provided for eliminating stale odors within automobiles by drying the internal components of the air conditioning system after the system has been switched off. Because of the simple assumptions built into the method of this invention for determining when the engine has been switched off and when the air conditioning system likely had been operated, the complexity of the invention is greatly reduced when compared to prior art solutions. Furthermore, and perhaps most importantly, the apparatus of the present invention operates with only three connections to the vehicle's electrical system. Specifically, connections are made only to the positive terminal of the vehicle's electrical system, to the blower of the air conditioning system, and to ground. Thus, the apparatus of this invention can be installed or retrofitted onto existing vehicles by virtually any automotive mechanic without the need for specialized personnel. The connections are made quickly, easily, and inexpensively and the device itself is inexpensive because of the lack of highly specialized sensors, detectors, valve controllers and the like. As an added feature, and without any further connection to the automotive electrical system, the method and apparatus of the present invention checks to see that the battery of the vehicle has a sufficient charge to operate the blower before it will activate the blower. This ensures that if a vehicle's battery is weak or has an insufficient charge, blower operation will be bypassed so that the battery will not be drained by operation of the blower.

Thus, it is an object of this invention to provide a method and apparatus of drying the internal components of an automotive air conditioning system to prevent the buildup of fungus and its attendant odors.

Another object of the invention is to provide an afterblow control module that is simply and inexpensive to acquire and to install on existing vehicles.

A further object of the invention is to provide an afterblow control module that can be installed by virtually any automotive mechanic without specialized training or assistance.

These and other objects, features, and advantages of the present invention will become more apparent upon review of the detailed description set forth below when taken in conjunction with the accompanying drawings, which are briefly described as follows.

DETAILED DESCRIPTION OF THE PREFERRED EMBODIMENTS

Figure 1:
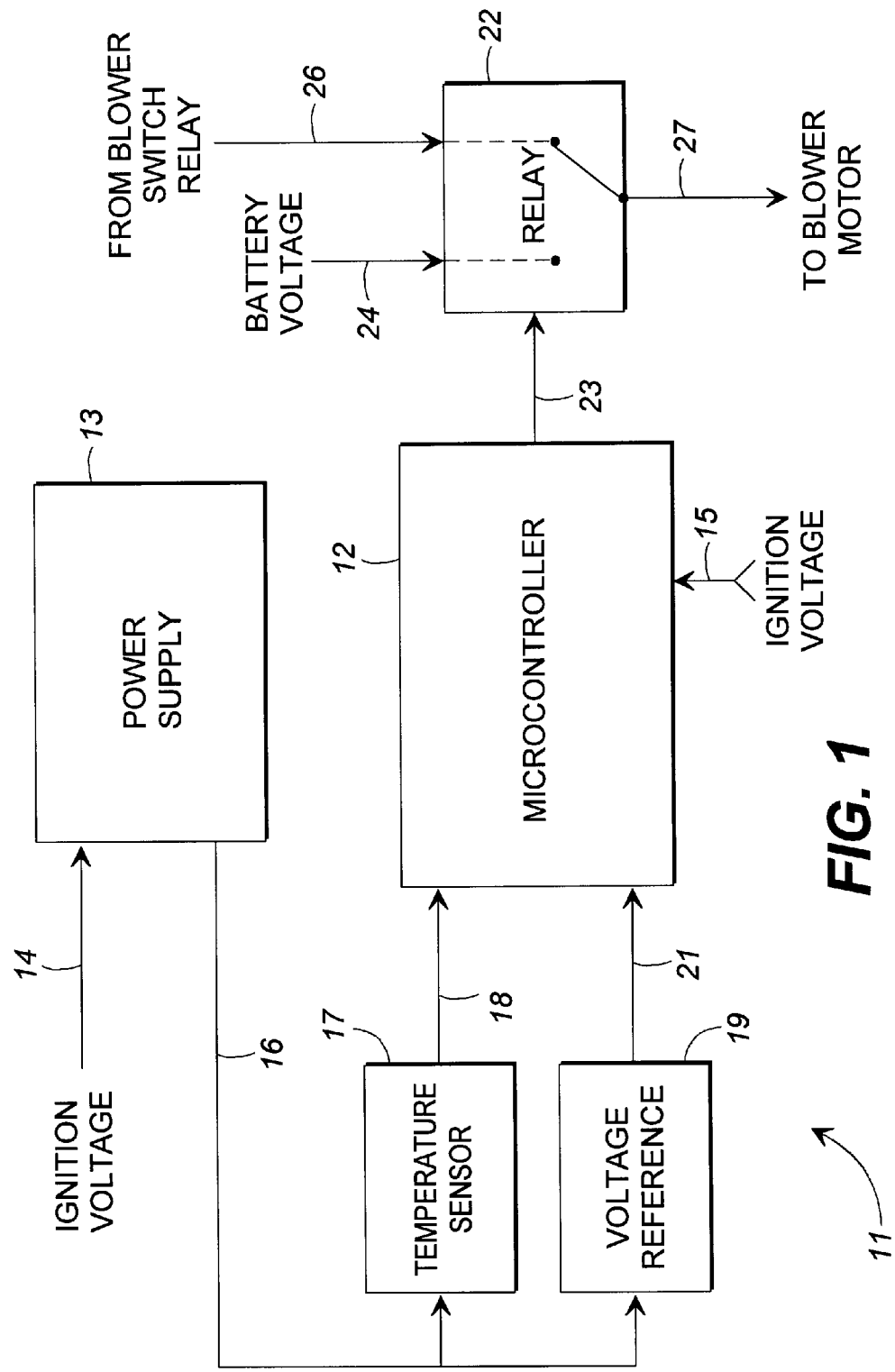
FIG. 1 is a functional block diagram illustrating the apparatus of the present invention in a preferred form.

Referring now in more detail to the drawings, in which like numerals refer to like parts throughout the several views, FIG. 1 is a block diagram illustrating the components of the present invention and their interconnection for performing the method of the invention. At the heart of the apparatus is an integrated circuit micro-controller 12 that is adapted to receive various signals, make decisions based upon the signals, and to send signals indicative of the decisions. In this case, the micro-controller 12 is powered by a power supply 13 that receives its power from the ignition voltage of the vehicle through a connection 14. The power supply 13 provides operating power for the micro-controller 12 and also provides power for various other electronic components of the apparatus.

The micro-controller 12 receives an analog voltage signal through connection 15 from the vehicle's ignition voltage system. As described in more detail below, the ignition voltage varies as a function of whether the vehicle's engine is operating or not. Specifically, if the vehicle's engine is operating and the battery is being charged by the alternator, the ignition voltage typically will be above 13 volts and usually about 13.2 volts. Conversely, when the engine is switched off, the ignition voltage drops to the value of the battery voltage, which is typically less than 13 volts.

The micro-controller 12 also receives an analog voltage signal through connection 18 from an integrated circuit temperature sensor 17. The temperature sensor 17 provides an analog voltage that is proportional to the ambient temperature in the vicinity of the vehicle. In this way, the micro-controller can determine the ambient temperature and this information is factored into decisions as described below. The micro-controller 12 is also coupled through connection 21 to a voltage reference 19. The voltage reference provides a steady reference voltage that does not vary with temperature, humidity, or whether the engine is running or not. The reference voltage is used by the micro-controller as a bench mark and the ignition voltage is compared to the reference voltage in order to determine precisely what the ignition voltage is at any particular time.

One of the output ports 23 of the micro-controller is coupled to a relay 22. The relay 22 preferably is a single pole double throw type relay with a common output 27 that is coupled to the blower motor of the vehicle's air conditioning and heating system. One of the input terminals of the relay 22 is coupled through connection 26 to the standard blower switch/relay line of the vehicle. Prior to installation of the present invention on a vehicle, this switch/relay line is hardwired directly to the blower motor and provides signals thereto for operating the blower at various speeds and under various conditions. In the normal configuration of the relay 22, the switch/relay line is coupled through the relay to the blower motor. Thus, when the relay is in its normal configuration as shown in FIG. 1, the blower motor operates in its normal way responding to signals from the cockpit switches and the vehicle's blower relay system.

The other input port of the relay 22 is coupled directly to the battery voltage through connection 24. When the relay is activated by an appropriate signal from the micro-controller, the connection is switched by the relay from the blower switch/relay pole directly to the battery voltage pole. This provides battery voltage directly to the blower motor, which causes the blower motor to operate at full speed as long as the relay is engaged. When the relay is again disengaged by an appropriate signal from the micro-controller, the normal connection is made between the blower motor and the vehicle's switch/relay system.

Figure 2:
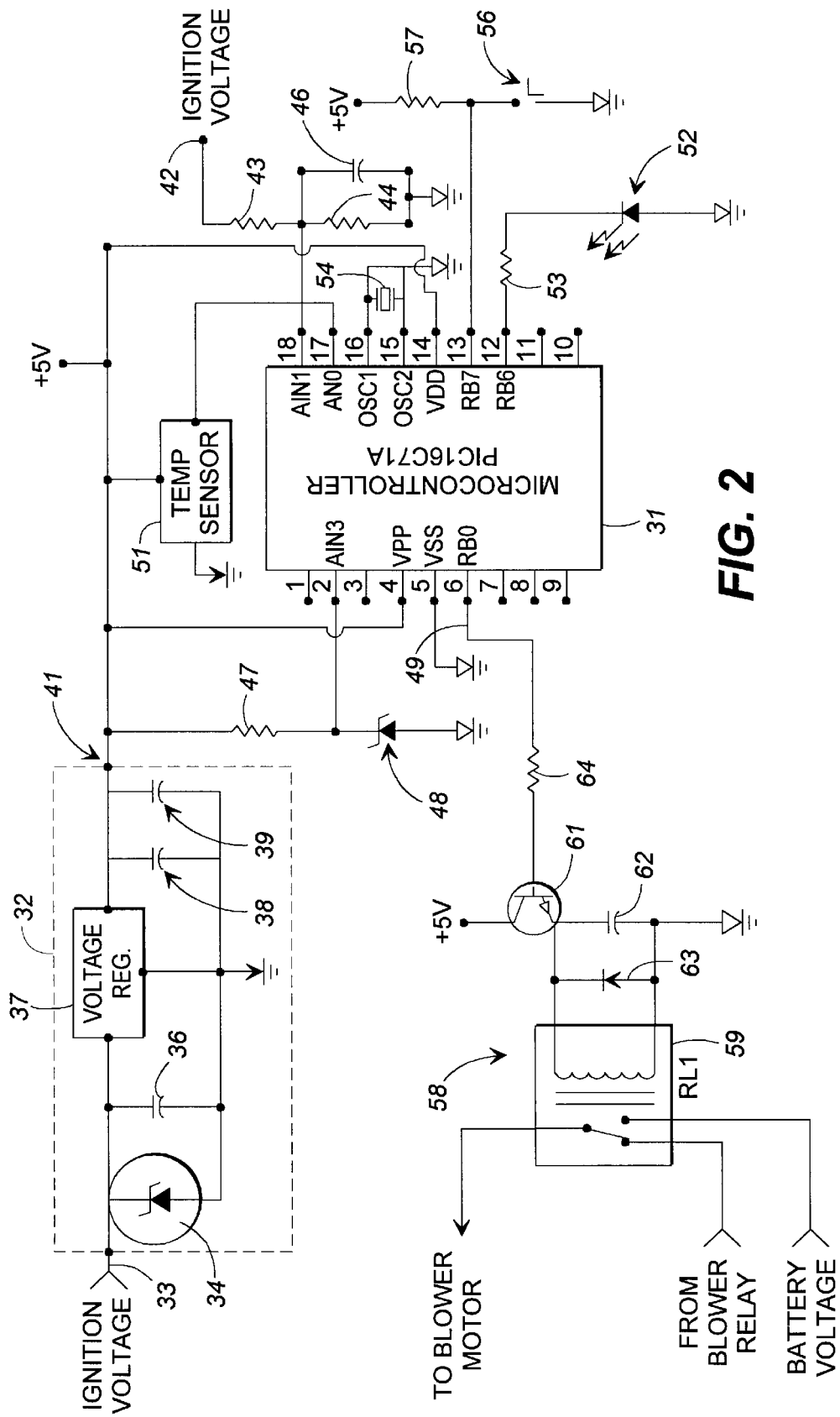
FIG. 2 is a detailed electronic schematic showing a preferred circuit for implementing the method of the present invention.

FIG. 2 is a detailed electronic schematic showing a preferred circuit for performing the method of the present invention. It will be understood by those of skill in the art that various additions, deletions, and modifications might be made to the preferred circuit illustrated in FIG. 2 and that the process of the present invention could be performed by a number of equivalent circuits. Accordingly, the circuit of FIG. 2 should be considered only a preferred exemplary embodiment and is presented for purposes of providing an enabling disclosure. Also, it should be noted that the components shown in FIG. 2 are labeled with different reference numerals than those in the block diagram of FIG. 1 for clarity and to permit the individual electronic components to be referred to separately from the functional blocks shown in FIG. 1.

The heart of the circuit shown in FIG. 2 is an integrated circuit micro-controller 31 that receives various signals from other components of the circuit, makes decisions based upon the signals, and controls the blower relay 59 in an appropriate manner. Preferably, the micro-controller is a Model PIC16C71A chip available from The MicroChip Corporation. However, other brands and models of micro-controllers might be substituted.

The micro-controller 31 is provided with an array of pins that comprise the input and output terminals of the micro-controller. For example, as used in the present invention, pins 2, 17, and 18 comprise analog input pins that receive analog voltages. Pins 4 and 14 receive operating voltage for providing power to the micro-controller and pin 5, in the configuration of FIG. 2, is connected to ground. Pins 15 and 16 of the micro-controller 31 receive clock signals from a crystal oscillator 34 and these clock signals are used to sequence the steps programmed into the micro-controller and to determine the lapse of real time. Pin 13 in the configuration of FIG. 2 is configured as a TTL input pin and pins 6 and 12 are configured as output pins that can be directed by the programming of the micro-controller to be set either to a high voltage state or a low voltage state to control external devices.

The circuit is provided with a power supply 32 that provides a nominal 5 volt operating power for the various integrated circuit components of the invention. The power supply 32 is conventional in nature and comprises a 5 volt voltage regulator 37 that preferably is a 5 volt linear regulator Model LM340T-5 available from National Semiconductor. The voltage regulator 37 is coupled to the ignition voltage of the vehicle through connection 33. A voltage suppressor 34 and a filter capacitor 36 are coupled between the ignition voltage line and ground in order to filter and regulate the input voltage to the voltage regulator 37 and thus provide a more consistent voltage level. Preferably, the suppressor 34 is a 15 volt transient voltage suppressor Model No. P6KE15CAGICT available from the Panasonic Corporation and the filter capacitor 36 is a standard 100 μf 25 volt 10% aluminum electrolytic capacitor available from a variety of suppliers.

The output of the voltage regulator 37 is a constant 5 volt supply potential available at the output 41. A pair of filter capacitors 38 and 39 are connected between the output of the voltage regulator 37 and ground in order to filter the output signal and to shunt any AC components of the signal to ground. Preferably, capacitor 38 is also a 100 μf 25 volt 10% aluminum electrolytic capacitor and capacitor 39 is a 0.01 μf 50 volt 10% monolithic capacitor. While the circuit comprising the power supply 32 of the present invention is relatively common, it will be understood that a variety of power supply circuits might be substituted for the illustrated embodiment as long as a steady 5 volt operating power is supplied by the chosen circuit.

The 5 volt output of the power supply 32 is coupled to pins 4 and 14 of the micro-controller 31 to provide operating power for the chip. Pin 5 of the micro-controller chip is coupled to ground through connection 49 to complete the operating power requirements of the chip. A Fahrenheit temperature sensor 51, which preferably is a Model LM34DZ available from National Semiconductor receives operating power from the power supply 32. The temperature sensor 51 provides an analog output voltage that is proportional to the temperature sensed by the temperature sensor. This output voltage is coupled to analog input pin 17 of the micro-controller 31. Accordingly, the micro-controller 31 can be programmed to interrogate pin 17, determine the voltage present at the pin, and, based upon a knowledge of the relationship between the voltage and temperature, determine the temperature sensed by the temperature sensor 51. Preferably, the temperature sensor 51 is placed away from artificial heat sources and in a region where the ambient temperature in the vicinity of the vehicle is sensed by the temperature sensor. In this way, the micro-controller 31 can determine the ambient temperature in the vicinity of the vehicle through interrogation of its analog input pin 17.

A crystal oscillator 54, which preferably is a 4.00 MHz crystal Model MP040 available from the CTS Corporation, is coupled between oscillator pins 15 and 16 of the micro-controller 31. The crystal 54 provides a constant 4 MHz signal to the oscillator pins and this signal is used as a clock source for the micro-controller and also to allow the micro-controller to determine the passage of real time.

Analog input pin 18 of the micro-controller is coupled to the vehicle's ignition voltage to allow the micro-controller to determine the voltage level of the ignition system upon interrogation of the input pin 18. The ignition voltage 42 is coupled to pin 18 through a voltage divider that comprises resistors 43 and 44. A filter capacitor 46 is also provided to filter out any AC components of the ignition voltage. Preferably, resistor 43 is a 56 Kohm 1% ¼ watt metal film resistor and resistor 44 is a 10 Kohm 1% ¼ watt metal film resistor. Capacitor 46 preferably comprises a 100 μf 25 volt 10% aluminum electrolytic capacitor. The purpose of the voltage divider network comprising resistors 43 and 44 and capacitor 46 is to scale the ignition voltage down to a range acceptable to the micro-controller at its analog input pin 18. Thus, the scaled down voltage received at pin 18 is directly proportional to the actual ignition voltage and the actual ignition voltage can be determined therefrom.

Analog input pin 2 of the micro-controller 31 is coupled to a reference voltage source that is steady and reliable. The reference voltage is used for comparing to other analog inputs and determining their value relative to the reference voltage. The reference voltage is supplied by means of a Zener diode 48 coupled through resistor 47 to the 5 volt supply voltage and to the analog input pin 2 of the micro-controller. Preferably, the diode 48 comprises a 2.5 volt voltage reference Zener diode Model LM336-2.5 available from the National Semiconductor Corporation, although other equivalent components might be substituted. The diode 48 in conjunction with the resistor 47 provides a constant reference voltage of 2.5 volts at analog input pin 2 and because of the characteristics of the Zener diode, this voltage is very stable and independent of any external influences that might otherwise cause the reference voltage to vary.

TTL input pin 13 of the micro-controller is connected to a test switch circuit, which comprises switch 56 and resistor 57. Preferably, resistor 57 is a 10 Kohm 1% ¼ watt metal film resistor connected between the 5 volt supply and pin 13. Accordingly, when the switch 56 is disengaged, pin 13 of the micro-controller is held in its high voltage state by the resistor 57. However, the pin 13 can be temporarily brought to its low voltage state by engagement of the switch 56. The change in state at pin 13 can be used by the micro-controller to indicate that the user desires a test procedure to be initiated to test the various operating aspects of the circuit.

Output pin 12 of the micro-controller is coupled through resistor 53 to a light emitting diode (LED) 52. Preferably, resistor 53 is a 1 Kohm 1% ¼ watt metal film resistor. With this arrangement, the LED 52 can be lit by the micro-controller by setting pin 12 to its high voltage state. Alternatively, the LED can be turned off by setting pin 12 to its low voltage state. In the present invention, LED 52 is used as an indicator to provide visual queues that the circuit is active as the process of the present invention is carried out.

TTL output pin 6 of micro-controller 31 is coupled through a resistor 64, a transistor 61, a filter capacitor 62, and a diode 63 to a relay 59 for controlling operation of the vehicle's blower. Resistor 64 preferably is a 1 Kohm 1% ¼ watt metal film resistor and transistor 61 can be any of a variety of common transistors capable of providing sufficient current for operating the relay 59. The filter capacitor 62 preferably is a 100 µf 25 volt 10% aluminum electrolytic capacitor and diode 63 preferably is a Model 1N4007 general purpose diode. With the configuration shown in FIG. 2, when the output pin 6 of the micro-controller is set to a high voltage state, the transistor 61 conducts current and engages the relay 59. Conversely, when the output pin 6 of the micro-controller is in a low voltage state, the transistor does not conduct current and the relay 59 is in its normal inactive state, as is illustrated in FIG. 2.

Relay 59 is a single pole double throw type relay and can be a Model T90S5D12-5 relay available from the Potter and Brumfield Corporation. In the configuration shown in FIG. 2, the output pole of the relay 59 is coupled to the blower motor of the vehicle's air conditioning system. One of the input poles is coupled to the normal blower switch/relay system of the vehicle and the other input pole of the relay is coupled to the battery. In its normal unactived configuration as shown in FIG. 2, it will be seen that the blower motor is coupled to the blower switch/relay system of the vehicle so that the blower operates in the normal way as it would if the relay were not installed. When the relay 59 is activated by the micro-controller 31, the blower motor is coupled directly to the battery of the vehicle. Thus, when the relay is activated, the blower is operated at its full speed until the relay is again deactivated.

Figure 3:
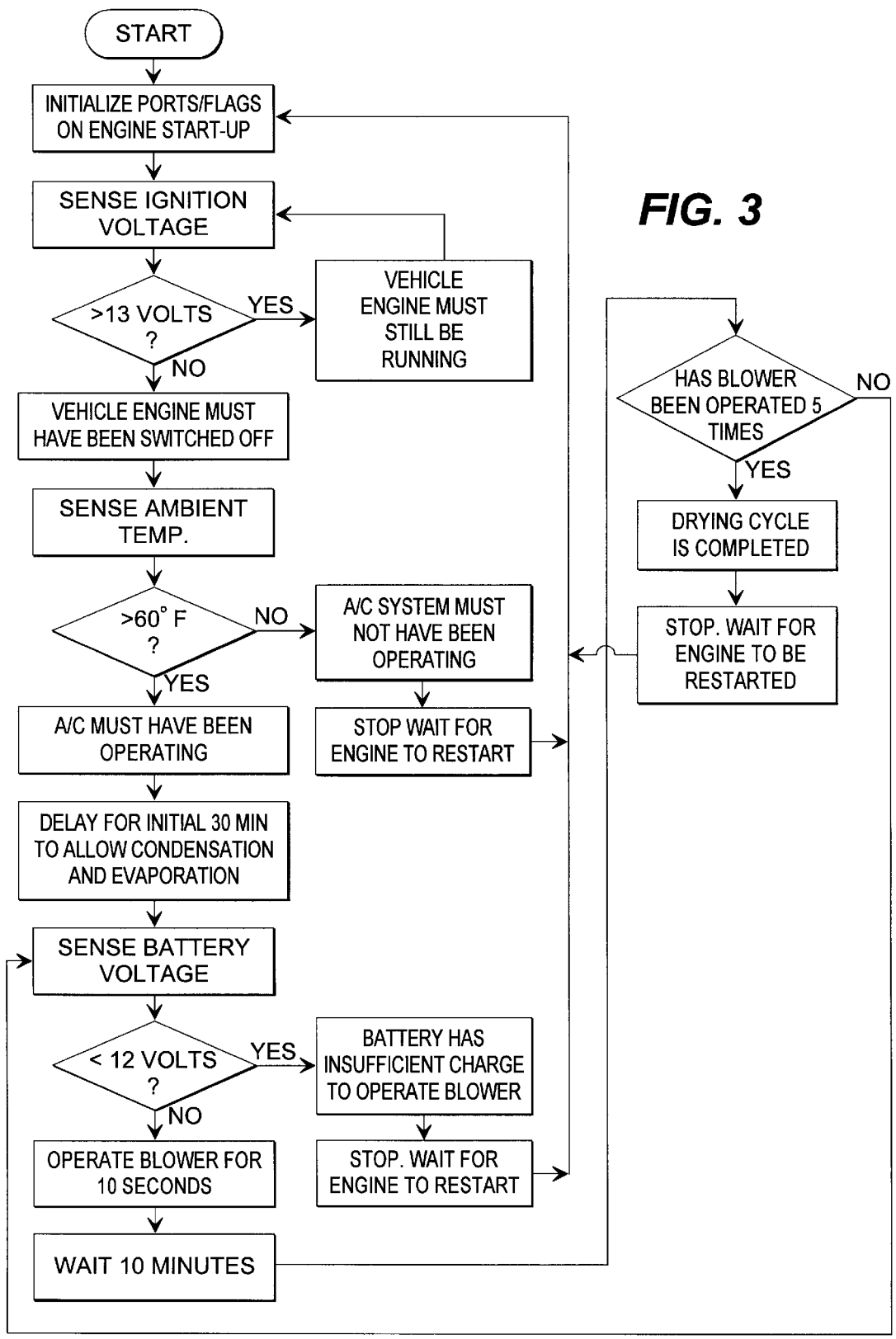
FIG. 3 is a detailed functional flow chart illustrating a preferred methodology for programming the micro-controller of the invention to carry out the process of the invention.

The micro-controller 31 shown in the schematic of FIG. 2 is programmed to perform the method of the present invention, as illustrated by the functional flow chart shown in FIG. 3. It should be understood that FIG. 3 illustrates one preferred series of steps for carrying out the process of the present invention. However, the steps could be performed in different orders and in different ways without departing from the spirit and scope of the invention.

In the preferred methodology of FIG. 3, the various ports and flags of the micro-controller 31 are first initialized when the engine of the vehicle is started. After the initialization process, the micro-controller senses the ignition voltage through its analog input pin 18 and asked whether the input voltage is greater than 13 volts. If the ignition voltage is greater than 13 volts, this indicates that the engine is still running and that the battery is being charged by the alternator. Under these conditions, the program within the micro-controller simply loops back and senses the ignition voltage again. As long as the voltage remains above 13 volts, this loop continues and no actions are taken by the circuit of the invention. When the ignition voltage drops below 13 volts, the program determines that the vehicle engine must have been switched off since it is no longer being charged by the alternator. Thus, the sensed voltage is compared to the predetermined threshold of 13 volts and a determination is made, based upon the results of the comparison, of whether the engine is running or has been switched off.

If it is determined that the vehicle engine has been switched off because the ignition voltage has fallen below 13 volts, the program within the micro-controller next senses the ambient temperature from the output of temperature sensor 51. If, as a result, it is determined that the ambient temperature is below 60 degrees Fahrenheit, a determination is made that the air conditioning system of the vehicle must not have been operating when the engine was running. This determination is based upon the assumption that under most circumstances, the air conditioning system will not be operated below 60 degrees. While such an assumption is not 100% accurate, it is nevertheless true in most cases and is more than sufficient for proper operation of the present invention. If a determination is made that the air conditioning system was not operating, the program stops and waits for the engine to restart, in which case control is returned to the initialization routine and the program is started over.

If it is determined that the ambient temperature is greater than 60 degrees Fahrenheit, a determination is made that the air conditioning system of the vehicle likely was operating when the engine was running. Again, this assumption is not 100% accurate but is more than sufficiently accurate for proper operation of the present invention.

At this point in the process, a first determination has been made that the engine has been switched off and that the air conditioning system was operating while the engine was running. These are the two conditions under which the process of the present invention functions to dry condensate from the heat exchanger of the vehicle's air conditioning system in order to remove moisture and thwart the growth of fungus and bacteria. This drying process is accomplished through operating the blower of the air conditioning system on a predetermined time schedule that has been demonstrated through experimentation to dry the heat exchanger adequately.

First, the program simply delays for an initial 30 minute period. This allows condensation that has formed on the heat exchanger and other surfaces within the air conditioning system to begin to evaporate and saturate the air within the duct work of the air conditioning system. After the initial 30 minute delay, the air within the duct work and in and around the heat exchanger is fully saturated with moisture as a result of the evaporation of the condensate.

Next, the battery voltage is sensed by the micro-controller through analog input pin 18 and the program asks whether the battery voltage is less than 12 volts. If the battery voltage is less than 12 volts, it is determined that the battery has an insufficient charge to operate the blower. In other words, operation of the blower under these conditions might drain the battery. Accordingly the blower will not be operated and the program will simply stop and wait for the engine to restart, whereupon control is returned to the initialization routines.

If the battery voltage is greater than 12 volts, then the battery has a sufficient charge to operate the blower. Accordingly, the program next operates the blower for 10 seconds by setting its output pin 6 to a high voltage state, which engages the relay 59 and connects the blower directly to the battery. The result is that the moisture laden saturated air within the ducts of the air conditioning system is removed and replaced by dry ambient air that is drawn through the exterior vents of the vehicle.

After the blower has initially been operated to remove the moisture laden air, a 10 minute delay is initiated to allow further evaporation of condensate. After the 10 minute delay, the program asks whether the blower has been operated 5 times and, if it has not, control is returned to the portion of the program that senses the battery voltage, determines that it is greater than 12 volts, and operates the blower for 10 seconds. Thus, it will be seen, that the predetermined time schedule of the preferred embodiment is a 30 minute delay followed by 5 cycles of blower operation for 10 seconds and delays of 10 minutes. If the battery voltage falls below 12 volts during any of these cycles, the next scheduled cycle will not be carried out and the method will be stopped. It has been found through experimentation that the predetermined time schedule illustrated in FIG. 3 is sufficient to dry condensate from the heat exchanger of the air conditioning system and from any surrounding surfaces and that the growth of fungus and bacteria is effectively thwarted.

After 5 cycles of delays and blower operation, the drying cycle of the present invention is completed. Thus, the program stops and waits for the engine to be restarted, whereupon control is returned again to the initialization routines as shown.

In practical operation, then, when a vehicle's air conditioning system has been operating and the engine of the vehicle is switched off, the blower will be operated according to the predetermined time schedule programmed into the micro-controller to dry moisture from the heat exchanger and from within the duct work of the air conditioning system. The method is completely autonomous and operates without any input from the vehicle's owner. Further, the process of this invention is superior to prior art devices and methods because it is based on simple assumptions that nevertheless are accurate most of the time. These assumptions allow the circuit of the invention to be much simpler than prior art solutions and, in particular, when retrofitting the device of this invention to an existing vehicle, only three input connections need be made. This offers distinct advantages over the prior art, which can require 7, 8, or more connections as well as special sensors and valves. Accordingly, the present invention can be installed by virtually any automotive mechanic without the need for special training.

The invention has been described herein in terms of preferred embodiments and methodologies. It will be obvious to those of skill in the art, however, that various additions, deletions, and modifications might well be made to the illustrated embodiments without departing from the spirit and scope of the invention as set forth in the claims.

We claim:

1. A method of drying condensate from the heat exchanger of a vehicle's air conditioning system to thwart the propagation of fungus and bacteria and its attendant odor, said method comprising the steps of:
    (a) determining that the engine of the vehicle has been switched off;
    (b) sensing the ambient temperature and determining that the air conditioning system of the vehicle was in operation prior to the engine being switched off if the sensed ambient temperature is greater than a predetermined threshold;
    (c) upon determining in step (b) that the air conditioning system was in operation, operating the blower of the vehicle's air conditioning system on a predetermined time schedule to draw air through the air conditioning system for drying condensate from interior surfaces thereof.

2. The method of claim 1 and wherein step (a) comprises sensing the ignition system voltage of the vehicle, comparing the sensed voltage to a predetermined threshold, and determining that the engine of the vehicle has been switched off if the ignition system voltage is less than the predetermined threshold.

3. The method of claim 2 and wherein the predetermined threshold is about thirteen volts.

4. The method of claim 1 and where in step (b) the predetermined threshold is about sixty degrees Fahrenheit.

5. The method of claim 1 and wherein step (c) further comprises determining that the battery of the vehicle has a sufficient charge to operate the blower prior to operating the blower to prevent fatal battery drain as a result of blower operation.

6. The method of claim 5 and wherein the step of determining that the battery of the vehicle has a sufficient charge to operate the blower comprises sensing the battery voltage, comparing the sensed voltage to a predetermined threshold, and determining that the battery has a sufficient charge if the sensed voltage exceeds the predetermined threshold.

7. The method of claim 1 and wherein step (c) comprises delaying for an initial delay period to allow evaporation of the condensate, and operating the blower for a predetermined length of time to remove the evaporated condensate from the air conditioning system.

8. The method of claim 7 and further comprising waiting for a predetermined time after initial blower operation to allow further evaporation of condensate from the heat exchanger, and operating the blower again for a predetermined time to remove the evaporated condensate from the air conditioning system.

9. The method of claim 8 and wherein the steps of waiting for a predetermined time and operating the blower again for a predetermined time are repeated for a predetermined number of cycles.

10. The method of claim 9 and wherein the initial delay period is about thirty minutes, the wait times are about ten minutes, and the blower is operated for about ten seconds during each of the predetermined number of cycles.

11. The method of claim 9 and further comprising the step of determining that the battery of the vehicle has a sufficient charge before operating the blower.

12. The method of claim 11 and wherein the step of determining that the battery of the vehicle has a sufficient charge comprises sensing the battery voltage, comparing the sensed voltage to a predetermined threshold, and determining that the battery has a sufficient charge if the sensed voltage exceeds the threshold.

13. An apparatus for attachment to the air conditioning system of a vehicle to dry condensate from the heat exchanger of the air conditioning system and thereby to prevent propagation of fungus and bacteria and resulting odors, said apparatus comprising:

means for determining that the engine of the vehicle has been switched off;

means for sensing the ambient temperature and determining that the air conditioning system of the vehicle was in operation prior to the engine being switched off if the ambient temperature is greater than a predetermined threshold; and means for operating the blower of the vehicle's air conditioning system on a predetermined time schedule upon determining that the air conditioning system was in operation to draw air through the heat exchanger of the air conditioning system for drying condensate from the surfaces thereof.

14. The apparatus of claim 13 and wherein said means for determining that the engine of the vehicle has been switched off comprises means for sensing the ignition voltage of the vehicle, means for comparing the sensed voltage to a predetermined threshold, and means for determining that the engine has been switched off if the sensed voltage falls below the predetermined threshold.

15. A method of drying condensate from interior surfaces of a vehicle air conditioning system after operation of the system to thwart the propagation of fungus and bacteria and its attendant odor, said method comprising the steps of:

(a) sensing that the vehicle's battery has transitioned from a charging state to a discharging state as an indication that the vehicle's engine has been switched off;

(b) determining that the air conditioning system of the vehicle was in operation prior to the engine being switched off; and (c) operating the blower of the vehicle's air conditioning system on a predetermined time schedule to draw air through the air conditioning system to promote drying of interior surfaces thereof.

16. The method of claim 15 and wherein step (a) comprises monitoring the voltage of the vehicle's ignition system and determining that the transition has occurred when the monitored voltage drops from a first value higher than a predetermined voltage threshold to a second value lower than the predetermined voltage threshold.

17. The method of claim 16 and wherein the predetermined voltage threshold is about 13 volts.

18. The method of claim 18 and wherein step (b) comprises sensing the ambient temperature, comparing the sensed ambient temperature to a predetermined temperature threshold, and determining that the vehicle's air conditioning system had been operating if the sensed ambient temperature is greater than the predetermined temperature threshold.

19. The method of claim 18 and wherein the predetermined temperature threshold is about 60 degrees Fahrenheit.

* * * * *